United States Patent [19]

Sato et al.

[11] Patent Number: 5,403,720

[45] Date of Patent: Apr. 4, 1995

[54] METHOD FOR RAPID MEASUREMENT OF LIVING MICROORGANISMS AND MEASURING KIT

[75] Inventors: Mikio Sato; Futoshi Kawane, both of Sodegaura, Japan

[73] Assignee: Idemitsu Kosan Company Limited, Tokyo, Japan

[21] Appl. No.: 162,790

[22] Filed: Dec. 6, 1993

Related U.S. Application Data

[63] Continuation of Ser. No. 723,924, Jul. 1, 1991, abandoned.

[30] Foreign Application Priority Data

Jul. 11, 1990 [JP] Japan .................................. 2-181667
Jan. 30, 1991 [JP] Japan .................................. 3-027636

[51] Int. Cl.$^6$ ........................ B01D 61/14; C12N 1/02; C12M 3/06
[52] U.S. Cl. ............................... 435/31; 435/29; 435/30; 436/177; 436/825; 436/826; 210/294; 210/295; 210/299; 210/348; 210/506; 210/500.1; 210/510.1
[58] Field of Search .......................... 435/29, 30, 31; 436/174, 177, 825, 826; 210/294, 295, 299, 348, 506, 500.1, 510.1, 639

[56] References Cited

U.S. PATENT DOCUMENTS 4,336,337 6/1982 Wallis ....................................... 435/34
4,731,260 3/1988 Balding .......................... 210/500.23

FOREIGN PATENT DOCUMENTS 57-74095 5/1982 Japan .
62-138185 6/1987 Japan .
1-124767 5/1989 Japan .

OTHER PUBLICATIONS

Wallis et al. Applied & Env. Microbiology vol. 49 No. 5, pp. 1251-1253 (1985).
Patent Abstracts of Japan, vol. 15, No. 56 (C-804)(4584) Feb. 8, 1991, of JP-A-22 86 098 (Meidensha Corporation) Nov. 26, 1990.
C. Wallis et al, "Colorimetric Method for Rapid Determination of Bacteriuria", vol. 14, No. 3, 1981, Washington, D.C., USA, pp. 342-346, Journal of Clinical Microbiology.

*Primary Examiner*—Michael G. Wityshyn
*Assistant Examiner*—Jane Williams
*Attorney, Agent, or Firm*—Frishauf, Holtz, Goodman & Woodward

[57] ABSTRACT

A method for measuring the number of living microorganisms in a specimen which comprises entrapping the microorganisms on a hydrophobic filter after the dyeing thereof, or alternatively dyeing the microorganisms after entrapping them on the hydrophobic filter, removing excessive coloring matter by washing, and then determining the number of the microorganisms by the degree of coloration thereof. A kit for measuring the number of living microorganisms which comprises a hydrophobic filter, a syringe to which the filter is fittable, a coloring matter solution, a cleaning solution, and a color reference table. The present invention enables the rapid and convenient measurement of the number of living microorganisms in the specimen without use of special equipment. In accordance with the present invention, the measurement is usually completed within ten minutes.

18 Claims, 1 Drawing Sheet

METHOD FOR RAPID MEASUREMENT OF LIVING MICROORGANISMS AND MEASURING KIT

This application is a continuation of application Ser. No. 07/723,924, filed Jul. 1, 1991, now abandoned.

BACKGROUND OF THE INVENTION

1. Field of Invention

The present invention relates to a method for measuring, rapidly and in a simplified manner, the number of living microorganisms in a sample, and a measuring kit, which can be utilized in a wide variety of fields including metal working, paints and foodstuffs in which a problem of spoilage will arise, and in diagnostics for detecting bacteria in urine.

2. Background Information

Water-soluble metal working fluids such as cutting fluids, rolling coolants or polymer quenchants, liquid foodstuffs such as liquid flavoring matters, liquid foods and drinks or alcohols, water-soluble paints, and the like are used under conditions suitable for growth of microorganisms. Thus, depending on the degree of administration, such fluids are sometimes spoiled as a result of considerable growth of microorganisms.

In order to prevent spoilage of such water-soluble metal working fluids or liquid foodstuffs at an earlier stage and to keep them in a desirable state, it is necessary to know the exact number of microorganisms, particularly living aerobic bacteria in the sample.

For measurement of the number of living aerobic microorganisms such as yeasts and bacteria in various specimens, there has heretofore been known a method, for example, in which a predetermined amount of specimen is cultivated on an agar medium, the number of colonies formed are counted, and from the number of colonies, the number of living microorganisms is calculated.

This method, however, has disadvantages in that special equipment, such as an incubator, is needed, and a long time, usually 48 hours, is needed until the results of measurement are obtained.

Thus, for rapid measurement of living aerobic microorganisms, a method in which enzyme activity (catalase activity) is measured (Japanese Patent Application Laid-Open No. 74095/1982), and a method in which microorganisms are dyed with fluorescent coloring matter (Japanese Patent Application Laid-Open No. 138185/1987) were proposed.

However the former method has a problem that hydrogen peroxide has to be used, which is unstable. For the latter method, special equipment, such as a fluorescent photometer, is needed and, therefore, the method can be employed only in specified conditions.

Thus there was proposed a method in which microorganisms are adsorbed on a negatively charged filter and then dyed with coloring matter (Japanese Patent Application Laid-Open No. 124767/1989).

This method, however, has various disadvantages. For example, in the adsorption of microorganisms on the filter, pretreatment with a strong acid of pH 1-3 is needed, and the operation is very complicated; for example, caution should be taken to prevent the strong acid, such as hydrochloric acid, from coming into contact with the skin of an operator, and for removal of excessive free coloring matter, washing should be carried out at least twice.

In addition, U.S. Pat. No. 4,336,337 discloses an apparatus in which urine, for example, is dyed with safranine in the presence of EDTA and adsorbed on a positively charged filter and, thereafter, after washing with a cleaner of pH 2.7–4.0, the number of living microorganisms is determined according to the intensity of color.

In this case, however, a vacuum pump or equipment for suction is needed for removal of excessive coloring matter, and thus the size of the apparatus becomes large and the place where the apparatus is to be located, is limited.

SUMMARY OF THE INVENTION

The present invention is intended to overcome the above problems. An object of the present invention is to provide a method for measuring rapidly and in a simplified manner the number of living microorganisms without use of specified equipment. Another object of the present invention is to provide a measuring kit.

The present invention relates to a method for measuring the number of living microorganisms in a specimen in which the microorganisms are grasped on a hydrophobic filter after dyeing or alternatively after grasping on the hydrophobic filter, the microorganisms are dyed, excessive dye is removed by washing, and based on the degree of coloration of the microorganisms, the number of living microorganisms in the specimen is determined.

The method of the present invention can be carried out with ease by the use of a kit for measuring the number of living microorganisms, comprising a hydrophobic filter, a syringe to which the filter can be fitted, a coloring matter solution, a cleaning solution, and a color reference table.

Figure 1:
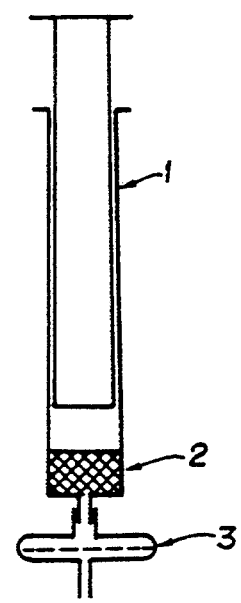
FIG. 1 is a perspective view illustrating a syringe fitted with the hydrophobic filter.

The FIG. 1, the reference numeral 1 indicates the syringe, the reference numeral 2 indicates the specimen, and the reference numeral 3 indicates the hydrophobic filter.

DETAILED DESCRIPTION OF THE INVENTION

The specimen to which the present invention is applicable, is not critical; the present invention can be applied to, for example, water-soluble metal working fluids such as cutting fluids, rolling coolants, and polymer quenchants; liquid foodstuffs such as liquid flavoring matters, liquid foods, and drinks, and alcohols; water-soluble paints; and further water such as river water, pond water, water in tanks, or waste water from homes.

Microorganisms which are measured according to the present invention include fungi, yeasts, bacteria, etc., particularly aerobic bacteria, existing in metal working fluids, paints, urine, etc.

In accordance with the method of the present invention, microorganisms in the specimen are dyed and then caught by the hydrophobic filter, or alternatively, after catching by the hydrophobic filter, the microorganisms are dyed. That is, the microorganisms are caught by the hydrophobic filter either before or after dyeing thereof.

In the dyeing of the microorganisms, various coloring matters are used, and a solution containing the coloring matter is added to the specimen either before or after seizing the microorganisms on the hydrophobic filter.

For this dyeing, any coloring matter can be used as long as it is capable of dyeing the microorganisms. For example, fuchsine, safranine, Victoria Blue, etc. can be used. From a viewpoint of ease of removal of excessive coloring matter, fuchsine and safranine are particularly preferred.

The coloring matter is used in the form of an aqueous solution (coloring matter solution). In preparing the coloring matter solution, ethanol, for example, can be added, if necessary.

The concentration of the coloring matter solution is usually in a range of 0.0005 to 2.0%, with the range of 0.002 to 1% being preferred. If the coloring matter concentration is less than 0.0005%, coloration is achieved only insufficiently. On the other hand, if it is more than 2.0%, excessive coloring matter becomes difficult to remove.

To the coloring matter solution, a surfactant may be added, if necessary. In this case, the amount of the surfactant added is 0.0001 to 1%.

In the preparation of the coloring matter solution, it is possible that a predetermined concentration of coloring matter solution is prepared in advance, and that the coloring matter solution is diluted with a cleaning solution, as described later, to the desired concentration.

The ratio of the amount of the coloring matter solution to that of the specimen solution is at least 1:1 and preferably at least 5:1. If the ratio is less than 1:1, poor coloration undesirably results.

As the hydrophobic filter, those made of polymers such as polytetrafluoroethylene, olefin-based polymers, and fluorine-based polymers can be used. In particular, polytetrafluoroethylene (trade name: Teflon) and olefin-based polymers are preferably used in that they permit easy removal of excessive coloring matter.

The pore diameter of the hydrophobic filter can be determined appropriately depending on the type of the microorganisms to be tested. For example, in the case of bacteria, the pore diameter is preferably 0.22 to 0.50 m$\mu$. The hydrophobic filter is not always critical in size; usually, since the hydrophobic filter is fitted to the syringe, its diameter is preferably in a range of 13 to 25 mm.

In connection with the color of the hydrophobic filter, a color permitting easy determination is chosen taking into consideration the color of the coloring matter to be used. For easy determination of the degree of coloration, a white filter is preferably used. In addition, a transparent filter and a translucent filter can be used. In the case of these filters, if the filter is placed on white paper, determination can be made easily.

The major feature of the present invention resides in that microorganisms in the specimen are caught by the use of the aforementioned hydrophobic filter.

Usually, the hydrophobic filter is fitted to the syringe, and the specimen which has been dyed or before dyeing is introduced into the syringe and then filtered under pressure through the hydrophobic filter to seize the microorganisms. When the specimen before dyeing is introduced, it is dyed with the coloring matter after the filtration.

From the specimen which has been dyed and seized on the hydrophobic filter is removed excessive coloring matter by washing. As this cleaning solution, water and various buffer solutions (of pH of about 6 to 8) can be used. In addition, various surfactants can be added, if necessary. In this case, the amount of the surfactant added is 0.0001 to 1%.

The amount of the cleaning solution used varies with the diameter of the hydrophobic filter; for example, when the diameter of the hydrophobic filter is 13 mm, the amount of the cleaning solution used is in a range of 1 to 5 ml, with the range of 2 to 3 ml being preferred. If the amount of the cleaning solution used is less than 1 ml, washing is achieved only insufficiently. On the other hand, if the amount of the cleaning solution used is more than 5 ml, the coloring matter may leak from the microorganisms. From a viewpoint of minimizing an error, it is preferred that the amount of the cleaning solution used in preparation of the color reference table and a calibration curve be made equal to that used in the washing of the unknown specimen.

In connection with the removal of the excessive coloring matter, for example, the cleaning solution as described above is introduced into the syringe in which the specimen dyed and seized on the hydrophobic filter is introduced, and then filtered under pressure to wash and remove the excessive coloring matter.

Based on the degree of coloration of the microorganisms in the specimen, which has been freed of the excessive coloring matter, the number of living microorganisms in the specimen is determined.

The number of living microorganisms is measured: (1) with the eye, or (2) by colorimetry based on the measurement of optical density (O.D.).

In accordance with the method (1) above in which the number of living microorganisms is visually determined, the degree of coloration, i.e., intensity of color of the microorganisms on the hydrophobic filter, is compared with the color reference table which has been previously prepared using specimens containing known numbers of living microorganisms.

The color reference table, which shows a relation between the number of living microorganisms in the specimen and the corresponding degree of coloration resulting from the dyeing thereof, can be prepared by taking color photographs of filters which have been dyed and washed according to the method of the present invention, except that the specimens containing known numbers of microorganisms have been used, or by dyeing filter papers, for example, with colors of the same intensity as the filters.

Depending on the accuracy of measurement of the unknown specimen, specimens containing known numbers of living microorganisms are chosen. It is usually said that if the number of living microorganisms is $1 \times 10^4$ to $1 \times 10^5$ per milliliter of the specimen, the specimen is not spoiled, whereas if it is more than $1 \times 10^7$, the specimen is spoiled. Thus, in determining the degree of spoilage of the specimen, it is sufficient to prepare the color reference table in which there are shown the corresponding colors at fours points, for example, of $1 \times 10^4$ or less, about $1 \times 10^5$, about $1 \times 10^6$, and $1 \times 10^7$ or more, all being per milliliter of the specimen.

When the color reference table is used, the hydrophobic filter, the syringe to which the hydrophobic filter is fittable, the coloring matter solution, and the cleaning solution are combined together to produce a measuring kit which enables to measure, rapidly and conveniently, the number of living microorganisms.

Any syringe can be used as long as it is capable of filtering under pressure in combination with the hydrophobic filter. The syringe may be made of either glass or plastics. The volume of the syringe can be determined appropriately depending on the amount of the cleaning solution, for example.

In accordance with the colorimetry based on the measurement of optical density (O.D.) of the method (2) above, the coloring matter attached onto the microorganisms which have been seized on the hydrophobic filter is eluted with an organic solvent, the elute thus obtained is measured in absorbance, and based on the absorbance, the number of living microorganisms is determined using the calibration curve of optical density vs. number of living microorganisms, which has been previously prepared. The absorbance can be determined appropriately depending on the type of the coloring matter to be used. Various alcohols can be used as the organic solvents, with ethanol being particularly preferred.

In the method of the present invention, the hydrophobic filter is used and, therefore, the problem that excessive coloring matter firmly attaches to the filter and is difficult to removed by washing, as encountered in the prior art methods, can be overcome. Accordingly, for removal of the excessive coloring matter, neither a vacuum pump nor suction equipment is needed, and a washing operation can be simplified.

The method of the present invention enables to measure the number of living microorganisms in the specimen, rapidly and conveniently, and further without use of special equipment. In accordance with the method of the present invention, the measurement is usually completed within 10 minutes.

The method of the present invention is applicable to all microorganisms including fungi, yeasts, and bacteria.

The measuring kit of the present invention is very simple and unexpensive, and furthermore, since no special equipment is needed, it can be used at any locations.

Accordingly, the present invention is greatly effective in measuring the number of living microorganisms growing in the specimen, particularly water-soluble metal working fluid, and thus it can be utilized in various fields such as metal working fluid paints and foodstuffs, both giving rise to a problem of spoilage, and diagnosis in which bacteria in urine cause problems.

The present invention is described in greater detail with reference to the following examples.

The calibration curve was prepared according to the method described below.

Preparation of Calibration Curve

Metal working fluid (microemulsion type) was diluted with the same fresh fluid to prepare specimens with various concentrations.

2 ml of a fuchsine solution prepared by diluting a fuchsine dyeing solution (concentration: 20 mg/100 ml) with a cleaning solution (PBS buffer solution with 0.0025% Tween 20 added, pH 7.8) to $\frac{1}{4}$ of the original concentration, was placed in a 5 ml volume tube, and 50 $\mu$l of the above specimens was introduced into the tube to dye aerobic bacteria contained therein.

After stirring for 1 to 2 seconds, the specimen was introduced into a 5 ml volume syringe barrel fitted with a TEFLON filter (trade name: DISMIC-13JP, produced by Advantech Toyo Co., Ltd.) having a diameter of 13 mm and then filtered under pressure to seize the aerobic bacteria on the Teflon filter. The state that the aerobic bacteria were seized on the filter, is shown in FIG. 1.

The syringe and the filter were separated from each other. After 2.5 ml of the same cleaning solution as used above was introduced into the syringe, the filter was again fitted to the syringe. The filter was washed with the cleaning solution by injecting it to thereby remove excessive coloring matter.

The coloring matter attaching onto the bacteria, which were seized on the filter fitted to the 5 ml volume syringe, was eluted with or dissolved in 1 ml of ethanol. Of the elute or solution thus obtained, a 200 $\mu$l (microliter) portion was placed on a 96 multiwell plate and measured for an optical density (O.D.) at 492 nm, as a degree of coloration, by the use of a microplate reader (produced by Corona Co., Ltd.).

On the other hand, the number of living aerobic bacteria in specimen solutions with various concentrations, which were identical to the above prepared specimens, was calculated by the agar plate method. That is, a predetermined amount of the specimen solution was inoculated onto a medium containing 0.5% of meat extract, 1.0% of peptone, 0.5% of sodium chloride, and 1.5% of agar (pH 7.0), cultivated at 30° C. for 48 hours, and from the number of colonies formed, the number of the living aerobic bacteria was determined.

Figure 2:
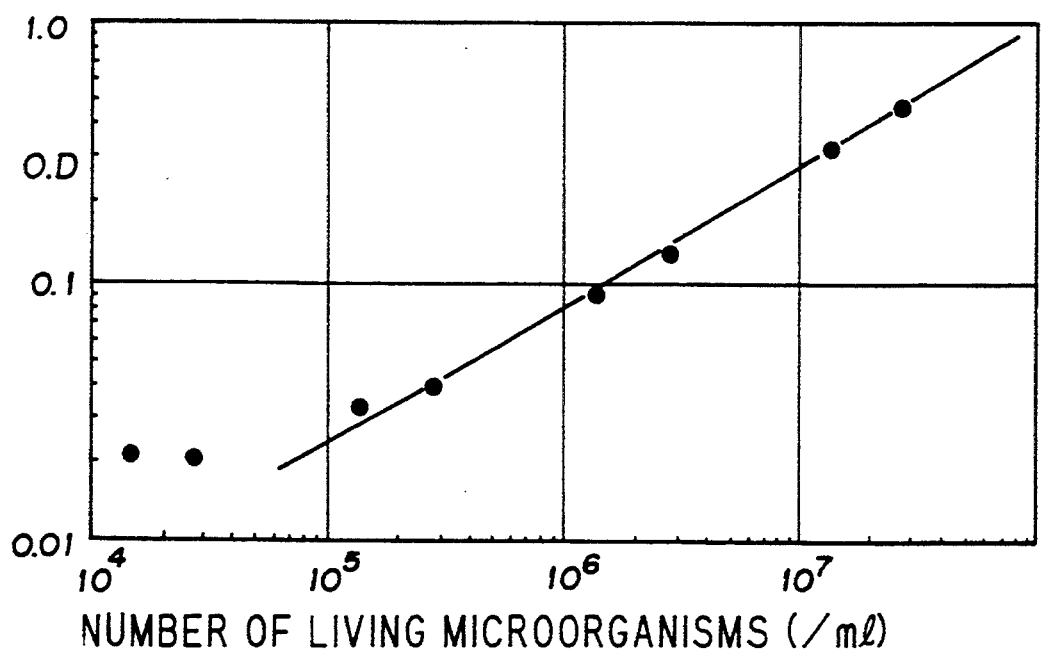
FIG. 2 is a calibration curve used in the examples of the present invention.

Based on the above results, the calibration curve of number of living microorganisms vs. optical density was prepared. This calibration curve is shown in FIG. 2.

Example 1

2 ml of a fuchsine solution obtained by diluting a fuchsine dyeing solution (concentration: 20 mg/100 ml) with a cleaning solution (PBS buffer solution with 0.0025% of Tween 20 added thereto, pH 7.8) to $\frac{1}{4}$ of the original concentration, was placed in a 5 ml volume tube, and 50 $\mu$l of metal working fluid B (microemulsion type) was introduced thereinto to dye aerobic bacteria.

After stirring for 1 to 2 seconds, the solution was introduced into a 5 ml volume syringe barrel fitted with a Teflon filter (trade name: DISMIC-13JP, produced by Advantech Toyo Co., Ltd.) having a diameter of 13 mm, and then filtered under pressure to seize the aerobic bacteria on the Teflon filter (see FIG. 1).

The syringe was separated from the filter, and 2.5 ml of the same cleaning solution as used above was introduced into the syringe. The filter was again fitted to the syringe, and excessive coloring matter was removed by washing with the cleaning solution.

The coloring matter attaching onto the bacteria which were seized on the filter fitted to the above 5 ml volume syringe, was eluted with or dissolved in 1 ml of ethanol. Of the solution thus obtained, a 200 $\mu$l portion was placed on a 96 multiwell plate and measured for optical density at 492 nm, as a degree of coloration, by the use of a microplate reader (produced by Corona Co., Ltd.).

The optical density of the elute or solution was 0.665, and the number of aerobic bacteria as determined with the calibration curve was $5.0 \times 10^7$/ml. The number of living bacteria in the same specimen as above, as determined by the agar plate method, for comparison, was $2.3 \times 10^7$/ml.

Examples 2 to 5

In the same manner as in Example 1, different types of metal working fluids were measured for optical density, and from the calibration curve shown in FIG. 2, the number of aerobic bacteria were determined. The results are shown in Table 1. For comparison, the results obtained by the agar plate method are shown in Table 1.

TABLE 1

| Example | Type of Metal Working Fluid* | Method of the Invention (/ml) | Agar Plate Method (/ml) |
| --- | --- | --- | --- |
| 2 | C | $5.5 \times 10^5$ | $4.8 \times 10^5$ |
| 3 | D | $4.0 \times 10^6$ | $2.6 \times 10^6$ |
| 4 | E | $5.0 \times 10^6$ | $5.9 \times 10^6$ |
| 5 | F | $1.0 \times 10^8$ | $2.0 \times 10^8$ |

*Type of Metal Working Fluid
C,E: Emulsion type
D: Soluble type
F: Microemulsion type Example 6

(1) Preparation of Color Reference Table

Metal working fluid A in which the number of living bacteria was known, was diluted with a fresh fluid to prepare standard samples containing living bacteria in the number of: (1) $10^7$/ml or more; (2) about $10^6$/ml; (3) about $10^5$/ml; and (4) $10^4$/ml or less. For these samples, the same operation as in Example 1 was applied until the step of removal of the excessive coloring matter by washing.

Thereafter, the degree of coloration of the aerobic bacteria on the hydrophobic filter was examined with the eye. The results were as follows:

| Standard Sample | Degree of Coloration |
| --- | --- |
| (1) | Strong |
| (2) | Somewhat strong |
| (3) | Weak |
| (4) | Very weak or no coloration |

Color photographs of the filters were taken to prepare the color reference table. The number of living bacteria contained in each standard sample was confirmed by the agar plate method.

(2) Determination of Number of Living Bacteria

For the metal working fluids B to F used in Examples 1 to 5, metal working fluid G (microemulsion type), and metal working fluid H (soluble type), the same operation as in Example 1 was applied until the step of removal of the excessive coloring matter by washing.

Thereafter, the degree of coloration of aerobic bacteria on the hydrophobic filter was examined with the eye, and by comparison with the color reference table, the number of aerobic bacteria was determined. The results are shown in Table 2. For comparison, the results obtained by the agar plate method are shown in Table 2.

TABLE 2

| Type of Metal Working Fluid | Method of the Invention (/ml) | Agar Plate Method (/ml) |
| --- | --- | --- |
| B | more than $1 \times 10^7$ | $2.3 \times 10^7$ |
| C | $1 \times 10^5$ | $4.8 \times 10^5$ |
| D | $1 \times 10^6$ | $2.6 \times 10^6$ |
| E | $1 \times 10^6$ | $5.9 \times 10^6$ |
| F | more than $1 \times 10^7$ | $2.0 \times 10^8$ |
| G | less than $1 \times 10^4$ | 0 |
| H | less than $1 \times 10^4$ | $1.1 \times 10^4$ |

Example 7

According to the same operation as in Example 1 except that an olefin-based filter (trade name: Chromatodisk 13AI, produced by Kurabo Co., Ltd.) was used in place of the Teflon filter as the hydrophobic filter, the number of living bacteria of the metal working fluid B (emulsion type) was determined. The optical density was 0.510, and the number of living aerobic bacteria as determined by the calibration curve was $3.0 \times 10^7$/ml. The number of living bacteria in the same specimen as above, as determined by the agar plate method, for comparison, was $2.3 \times 10^7$/ml.

Example 8

100 μl of metal working fluid B (microemulsion type) was diluted with 1 ml of water. Of the solution thus prepared, a 0.5 ml portion was filtered under pressure through the same filter as used in Example 1 (Teflon filter fitted with a 5 ml volume syringe barrel) to seize aerobic bacteria on the filter.

Then, 2 ml of the same fuchsine solution as used in Example 1 was introduced into the above 5 ml volume syringe, and passed under pressure through the filter to dye the aerobic bacteria.

Then, 2.5 ml of the same cleaning solution as used in Example 1 was introduced into the above 5 ml volume syringe, and passed under pressure through the filter to remove excessive coloring matter.

The coloring matter attaching onto the microorganisms, which were seized on the filter fitted to the above 5 ml volume syringe, was eluted with or dissolved in 1 ml of ethanol. Of the elute or solution thus obtained, a 200 μl portion was placed on a 96 multiwell plate and measured for optical density at 492 nm, as a degree of coloration, by the use of a microplate reader (produced by Corona Co., Ltd.).

The optical density was 0.546, and the number of living aerobic bacteria as determined by the calibration curve was $3.6 \times 10^7$/ml. The number of living bacteria as determined by the agar plate method for comparison was $2.3 \times 10^7$/ml.

Example 9

150 μl of each of river water, pond water, water in a water tank in which gold fishes were being fed, and waste water from home, coming into the active sludge processing unit, was treated in the same manner as in Example 1 until the step of removal of excessive coloring matter by washing with the cleaning solution.

Then, the degree of coloration of aerobic bacteria on the hydrophobic filter was examined with the eye, and by comparison with the color reference table prepared in Example 6(1), the number of living bacteria was determined. The results are shown in Table 3. The results obtained by the agar plate method for comparison are also shown in Table 3.

TABLE 3

| Sample | Method of the Invention (/ml) | Agar Plate Method (/ml) |
| --- | --- | --- |
| River water | $1 \times 10^5$ | $2.1 \times 10^5$ |
| Pond water | less than $1 \times 10^4$ | $1.6 \times 10^3$ |
| Tank water | $1 \times 10^6$ | $2.3 \times 10^6$ |
| Waste water | $1 \times 10^5$ | $5.6 \times 10^5$ |

What is claimed is:

1. A method for measuring the number of living microorganisms selected from the group consisting of fungi, yeast and bacteria in a specimen solution which comprises dyeing the microorganisms selected from the group consisting of fungi, yeast and bacteria with a water-soluble coloring matter solution, the water-soluble coloring matter being in a concentration of 0.0005 to 2.0% and entrapping the dyed microorganisms on a hydrophobic filter made of polytetrafluoroethylene, or alternatively entrapping the microorganisms on said hydrophobic filter and dyeing the entrapped microorganisms with said coloring matter solution, removing excessive coloring matter solution by washing with a washing solution consisting essentially of (i) water or a buffer solution, having a pH of 6 to 8 and (ii) 0.0001 to 1% of a surfactant, and then determining the number of the microorganisms by the degree of coloration thereof.

2. The method as claimed in claim 1, wherein the coloring matter which is attached to the microorganisms is eluted with an organic solvent, and the degree of coloration of the elute is measured for optical density and determined by colorimetry with reference to a calibration curve.

3. The method as claimed in claim 1, wherein the specimen is water-soluble metal working fluid.

4. The method as claimed in claim 1, wherein the microorganisms are aerobic bacteria.

5. The method as claimed in claim 1, wherein the coloring matter is fuchsine or safranine.

6. A kit for measuring the number of living microorganisms selected from the group consisting of fungi, yeast and bacteria in a specimen solution which comprises a hydrophobic filter made of polytetrafluoroethylene,
a syringe to which the filter is fittable,
a water-soluble coloring matter solution, the water-soluble coloring matter being in a concentration of 0.0005 to 2.0%,
a washing solution consisting essentially of (i) water or a buffer solution having a pH of 6 to 8 and (ii) 0.0001 to 1% of a surfactant, and
a color reference table.

7. The kit as claimed in claim 6, wherein the coloring matter solution is fuchsine dyeing solution or safranine dyeing solution.

8. The kit as claimed in claim 6, which is used for measuring the number of living aerobic bacteria.

9. The method as claimed in claim 1, wherein the entrapping and washing are carried out by filtration under pressure.

10. The method as claimed in claim 1, wherein the specimen is selected from the group consisting of a liquid foodstuff, a water-soluble paint and water.

11. The method as claimed in claim 2, wherein the ratio of the amount of the coloring matter solution to that of the specimen solution is at least 1:1.

12. The method as claimed in claim 11, wherein the concentration of the coloring matter solution is 0.002 to 1%; and the ratio of the amount of the coloring matter solution to that of the specimen solution is at least 5:1.

13. The method as claimed in claim 12, wherein the coloring matter solution is selected from the group consisting of a fuchsine dyeing solution, a safranine dyeing solution and a Victoria Blue dyeing solution; and the specimen is selected from the group consisting of a water-soluble metal working fluid, a liquid foodstuff, a water-soluble paint and water.

14. The method as claimed in claim 13, wherein the coloring matter solution is selected from the group consisting of a fuchsine dyeing solution and a safranine dyeing solution; the microorganisms are aerobic bacteria; and the entrapping and washing are carried out under pressure.

15. The method as claimed in claim 2, wherein the hydrophobic filter has a pore diameter of 0.22 to 0.50 m$\mu$ and the microorganisms are bacteria.

16. The method as claimed in claim 15, wherein the washing solution is in an amount of 1 to 5 ml.

17. The method as claimed in claim 16, wherein the specimen is a water-soluble working fluid; the coloring matter is fuchsine or safranine and the microorganisms are aerobic bacteria.

18. The kit as claimed in claim 7, wherein the hydrophobic filter has a pore diameter of 0.22 to 50 m$\mu$.

* * * * *